United States Patent [19]

Schneider et al.

[11] 4,308,278
[45] Dec. 29, 1981

[54] ANOREXIGENIC 4-[(3,4-DIALKOXYPHENYL)ALKYL]-2-IMIDAZOLIDINONE DERIVATIVES

[75] Inventors: Géza Schneider; Ferenc Andrási; Pál Berzsenyi; Árpád Lázár; Sándor Elek; István Elekes; István Polgári, all of Budapest, Hungary

[73] Assignee: Gyogyszerkutato Intezet, Budapest, Hungary

[21] Appl. No.: 90,450

[22] Filed: Nov. 1, 1979

[30] Foreign Application Priority Data

Jan. 11, 1978 [HU] Hungary ................ GO 1429

[51] Int. Cl.³ ................ A61K 31/415; C07D 233/38
[52] U.S. Cl. ................ 424/273 R; 548/317; 548/320
[58] Field of Search ................ 548/317, 320; 424/273 R

[56] References Cited

U.S. PATENT DOCUMENTS 3,636,039  1/1972  Gruenman et al. ................ 548/317
3,821,244  6/1974  Matier et al. ................ 548/322

OTHER PUBLICATIONS

Morrison et al., Organic Chemistry, 3rd Ed. Allyn & Bacon, Boston, 1974, pp. 283, 312–313.

*Primary Examiner*—Henry R. Jiles
*Assistant Examiner*—Natalia Harkaway
*Attorney, Agent, or Firm*—Young & Thompson

[57] ABSTRACT

4-[(3,4-Dialkoxyphenyl)alkyl]-2-imidazolidinone derivatives having the formula I

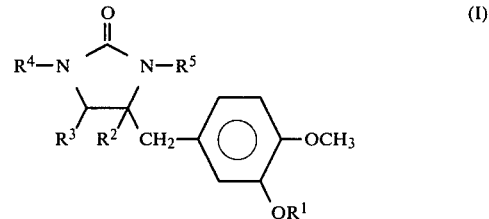

wherein
$R^1$ stands for a cycloalkyl group containing from 3 to 6 carbon atoms or benzyl group;
$R^2$ stands for hydrogen atom or an alkyl group containing from 1 to 4 carbon atoms;
$R^3$ stands for hydrogen atom or an alkyl group containing from 1 to 4 carbon atoms;
$R^4$ stands for hydrogen atom, or an alkyl group containing from 1 to 4 carbon atoms or an alkoxycarbonyl group containing from 1 to 4 carbon atoms; and
$R^5$ stands for hydrogen atom or an alkoxycarbonyl group containing from 1 to 4 carbon atoms, are prepared by (a) reducing a hydantoin derivative having the general formula II, wherein $R^1$ and $R^2$ are as defined above, with lithium aluminum hydride in a neutral organic solvent, or (b) hydrogenating catalytically an 1,3-dihydro-2H-imidazol-2-one derivative having the general formula III, wherein $R^1$ and $R^3$ are as defined above, while the meaning of $R^4$ is hydrogen atom or an alkyl group containing from 1 to 4 carbon atoms, or (c) reacting a carbamate derivative having the general formula IV, wherein $R^1$ is as defined above, while $R^6$ stands for an alkyl group containing from 1 to 4 carbon atoms, with an organic or inorganic base.

The compounds having the formula I possess valuable therapeutical properties, mainly anorexigenic activity.

2 Claims, No Drawings

ANOREXIGENIC 4-[(3,4-DIALKOXYPHENYL)ALKYL]-2-IMIDAZOLIDINONE DERIVATIVES

This invention relates to new 4-[(3,4-dialkoxyphenyl)alkyl]-2-imidazolidinone derivatives.

More particularly, this invention relates to new 4-[(3,4-dialkoxyphenyl)alkyl]-2-imidazolidinone derivatives having the formula I

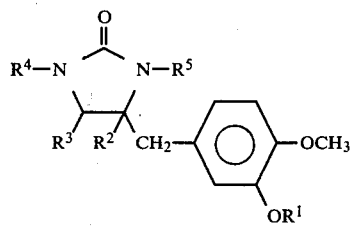

wherein
$R^1$ stands for a cycloalkyl group containing from 3 to 6 carbon atoms or benzyl group;
$R^2$ stands for hydrogen atom or an alkyl group containing from 1 to 4 carbon atoms;
$R^3$ stands for hydrogen atom or an alkyl group containing from 1 to 4 carbon atoms;
$R^4$ stands for hydrogen atom, or an alkyl group containing from 1 to 4 carbon atoms or an alkoxycarbonyl group containing from 1 to 4 carbon atoms, and
$R^5$ stands for hydrogen atom or an alkoxycarbonyl group containing from 1 to 4 carbon atoms.

Preferred representatives of the compounds having the formula I are those 4-[(3,4-dialkoxyphenyl)alkyl]-2-imidazolidinone derivatives wherein
$R^1$ stands for cyclopentyl or benzyl;
$R^2$ and $R^3$ each represent hydrogen atom; and
$R^4$ and $R^5$ each stand for hydrogen atom or methoxycarbonyl group.

It has been surprisingly found that the new 4-[(3,4-dialkoxyphenyl)alkyl]-2-imidazolidinone derivatives having the general formula I unexpectedly show an anorexigenic action. With exception of mazindole/5-(4-chlorophenyl)2,5-dihydro-3H-imidazo[2,1-a]izoindol-5-ol/, the anorexigenic drugs put on the market are amphetamine (D-benzethamine sulphate) derivatives and thus they show the adverse effects characteristic of amphetamine (euphoria, insomnia, depression on withdrawal) (Inpharma, November 27, 1976).

The aim of the invention is the preparation of anorexigenic compounds possessing a more favourable therapeutic ratio and different chemical structure, in comparison to the substances mentioned above.

The compounds having the formula I are new.

Compounds, which are similar in type to the substances prepared according to the invention, were reported in the German Offenlegungsschrift No. 1,921,685, pursuant to which these compounds exert a hypotensive and vasodilating effect. For the preparation a synthesis involving seven steps was presented. The first five steps consist of the Cope-Knoevenagel condensation and Darapsky's aminoacid synthesis (J. prakt. Chem. 146, 250/1936/), while the remaining two steps are analogous to the synthesis of 2-imidazolidinones published by Funke (Bull. Soc. Chim. France 1942, 806).

The disadvantages of this synthetic procedure are that it is tedious and, in addition to the numerous steps, the hydrogenation of the sixth step requires a specific catalyst (Raney cobalt), elevated temperature (110° C.) and high pressure (76 atm.).

It is known that 5,5-disubstituted hydantoins can be reduced by lithium aluminium hydride to 4,4-disubstituted-2-imidazolidinones (J. Am. Chem. Soc. 78, 3696/1956/), however, 5-monosubstituted hydantoins are not reduced to the appropriate 4-substituted-2-imidazolidinone derivatives (J. Org. Chem. 15, 1020/1950/).

Now it has been found that, by changing the reaction conditions, 5-monosubstituted hydantoins are also reduced to 4-substituted-2-imidazolidinone compounds. Principle of this process consists in that the hydantoin derivative is suspended in an ethereal solution of excess lithium aluminium hydride and tetrahydrofuran was gradually added to the mixture. In this way the hydantoin derivative, being insoluble in ether but readily soluble in tetrahydrofuran, gradually dissolves and is reduced in a good yield (72–87%) to the 2-imidazolidinone compound by lithium aluminium hydride which was present in excess in whole course of the reaction.

The 5-substituted hydantoin derivatives were obtained on the one hand by reduction with sodium amalgam of the benzylidenehydantoin compounds prepared by the condensation of the appropriate aromatic aldehyde with hydantoin, on the other hand by Bucherer-Bergs synthesis. The 5,5-disubstituted hydantoins were also synthetized by the latter process.

Thus, we have found a shorter synthetic route (consisting of four steps) for the preparation of 4-substituted-2-imidazolidinones having the formula I. This process is more simple and can be utilized widely.

We have prepared 4-substituted-2-imidazolidinone derivatives by the catalytic hydrogenation of 1,3-dihydro2H-imidazol-2-ones, too. According to the literature, this reduction was carried out in the presence of Adams catalyst; however, when the molecule contained a benzene ring, this latter was also saturated (J. Am. Chem. Soc. 68, 2350/1946/). Surprisingly, we have found that 4-dialkoxyphenyl-1,3-dihydro-2H-imidazol-2-ones could be hydrogenated to the appropriate 2-imidazolidinone derivatives in the presence of Adams catalyst, without saturation of the benzene ring.

Finally, we have obtained 4-substituted-2-imidazolidinones by the process of the German Offenlegungsschrift No. 1,921,685.

Compounds having the general formula I are prepared according to the invention (a) for preparing compounds having the formula I, wherein $R^1$ and $R^2$ are as defined above, while the meaning of $R^3$, $R^4$ and $R^5$ is hydrogen atom, by reducing a hydantoin derivative having the formula II

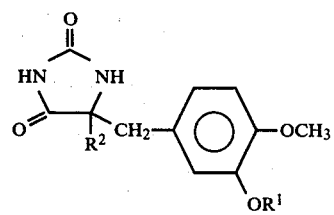

wherein $R^1$ and $R^2$ are as defined above, with lithium aluminium hydride in a neutral organic solvent, or (b) for preparing compounds having the formula I, wherein $R^1$ and $R^3$ are as defined above, while $R^2$ is hydrogen atom, $R^4$ is hydrogen atom or an alkyl group containing from 1 to 4 carbon atoms and $R^5$ means a hydrogen atom, by hydrogenating catalytically a 1,3-dihydro-2H-imidazol-2-one derivative having the formula III

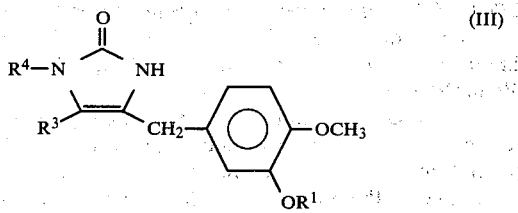

wherein $R^1$ and $R^3$ are as defined above, while the meaning of $R^4$ is hydrogen atom or an alkyl group containing from 1 to 4 carbon atoms, or (c) for preparing compounds having the formula I, wherein $R^1$ is as defined above, while $R^2$, $R^3$ and $R^4$ stand for hydrogen atom, by reacting a carbamate derivative having the formula IV

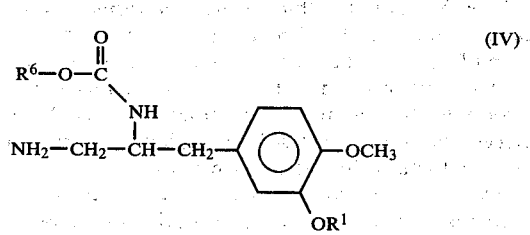

wherein $R^1$ is as defined above, while $R^6$ stands for an alkyl group containing from 1 to 4 carbon atoms, with an organic or inorganic base.

For preparing compounds having the formula I, wherein $R^1$, $R^2$ and $R^3$ are as defined above, while $R^4$ and $R^5$ stand for alkoxycarbonyl group containing from 1 to 4 carbon atoms, a 2-imidazolidinone derivative having the general formula I, wherein $R^1$, $R^2$ and $R^3$ are as defined above, while $R^4$ and $R^5$ stand for hydrogen atom, is reacted with alkyl trichloroacetate, or for preparing compounds having the formula I, wherein $R^2$, $R^3$, $R^4$ and $R^5$ are as defined above, while $R^1$ stands for a cycloalkyl group containing from 3 to 6 carbon atoms, a 2-imidazolidinone derivative having the formula I, wherein $R^2$, $R^3$, $R^4$ and $R^5$ are as defined above, while $R^1$ stands for a benzyl group, is catalytically hydrogenated and the product thus obtained is alkylated with a cycloalkyl halide containing from 3 to 6 carbon atoms.

According to a preferred embodiment of the invention the compounds having the formula I, wherein $R^1$ and $R^2$ are as defined above, while the meaning of $R^3$, $R^4$ and $R^5$ is hydrogen atom, are prepared by the reduction of a hydantoin derivative having the formula II, wherein $R^1$ and $R^2$ are as defined above, with 0.25-10 moles, preferably with 1.2-5 moles of lithium aluminium hydride in an ether, dioxane, hexamethylphosphoric acid triamide or 1,2-dimethoxyethane, preferably in a mixture of ether and tetrahydrofurane as solvent, at a temperature between 20° C. and 100° C., preferably between 60° C. and 65° C.

According to another preferred embodiment of the invention the compounds having thee formula I, wherein $R^1$ and $R^3$ are as defined above, while $R^2$ is hydrogen atom, $R^4$ is hydrogen atom or an alkyl group containing from 1 to 4 carbon atoms and $R^5$ means a hydrogen atom, are prepared by catalytic hydrogenation of a 1,5-dihydro-2H-imidazol-2-one derivative having the general formula III, wherein $R^1$ and $R^3$ are as defined above, while the meaning of $R^4$ is hydrogen atom or an alkyl group containing from 1 to 4 carbon atoms, in the presence of 5 to 100 percent of Adams catalyst in water, ethanol or a short-chain carboxylic acid, preferably in acetic acid as solvent.

According to a further process variant of the invention the compounds having the formula I, wherein $R^1$ is as defined above, while $R^2$, $R^3$, $R^4$ and $R^5$ each stand for hydrogen atom, are suitably prepared by reaction of a carbamate derivative having the formula IV, wherein $R^1$ is as defined above, while $R^6$ stands for an alkyl group containing from 1 to 4 carbon atoms, with an organic or inorganic base, preferably with an alkali hydroxide in aqueous or dry ethanol, preferably in water as solvent.

According to another process variant of the invention the compounds having the formula I, wherein $R^1$, $R^2$ and $R^3$ are as defined above, while $R^4$ and $R^5$ each stand for alkoxycarbonyl group containing from 1 to 4 carbon atoms, are suitably prepared by reaction of a 2-imidazolidinone derivative having the formula I, wherein $R^1$, $R^2$ and $R^3$ are as defined above, while $R^4$ and $R^5$ stand for hydrogen atom, with excess of an alkyl trichloroacetate, preferably of methyl or ethyl trichloroacetate, in a solvent boiling between 140° C. and 250° C., such as xylene, dimethyl formamide, dimethyl sulphoxide, preferably without any solvent, in an excess of alkyl trichloroacetate.

According to a further process variant of the invention the compounds having the formula I, wherein $R^2$, $R^3$, $R^4$ and $R^5$ are as defined above, while $R^1$ stands for a cycloalkyl group containing from 3 to 6 carbon atoms, are suitably prepared by catalytic hydrogenation of a 2-imidazolidinone derivative having the formula I, wherein $R^2$, $R^3$, $R^4$ and $R^5$ are defined as above, while $R^1$ stands for a benzyl group, and by subsequent alkylation of the product thus obtained with a cycloalkyl halide, preferably with a cycloalkyl bromide containing from 3 to 6 carbon atoms, in dimethyl formamide, dimethyl sulphoxide, a short-chain alkanol, or water, preferably in dimethylsulphoxide as solvent, in the presence of anhydrous sodium or potassium carbonate.

Preparation of the starting materials for the process of invention is described in the following papers: Berichte 67, 1214 (1934); J. Chem. Soc. Japan 53, 479 (1962); Z. physiol. Chem. 219, 233 (1933); J. Am. Chem. Soc. 77, 700 (1955); Berichte 49, 675 (1916); J. Am. Chem. Soc. 75, 2000 (1953); J. Org. Chem. 36, 829 (1971); J. Chem. Soc. 1924, 2283.

For studying the anorexigenic effect the following method was used. CFY rats were starved for 24 hours, then the substance was orally administered, and half an hour later the animals were allowed to feed ad libitum during 5 hours when the feed consumption was measured. The change in the body weight of animals and the amount of the consumed solid, granulated food or sugar milk or peeled potato, respectively, were determined. The $ED_{50}$ values were calculated from these data. The results obtained are summarized in Table I.

TABLE I

| Drug | ED$_{50}$* orally in rats, mg/kg | Acute LD$_{50}$ orally mg/kg in rats | Acute LD$_{50}$ orally mg/kg in mice | Therapeutic ratio |
|---|---|---|---|---|
| D-Amphetamine | 5.0 | 38[2] | 60[1] | 7.6 |
| Mazindol | 25.8[4] | 250 | 106 | 9.7 |
| Fenfluramine | 7.5 | 138[3] | 170–290[2] (100 i.p.) | 20.3 |
| Chlorphentermine | 12.5[5] | 375 | 250[5] | 30.0 |
| Ia | 10.5 | 760 | 2050 (680 i.p.) | 72.5 |

Notes to Table I:
[1] J. Med. Chem. 18, 71 (1975)
[2] E. Usdin: Psychotropic Drugs, 1972
[3] Arch. Int. Pharmacodyn. 200, 102 (1972)
[4] Informative Booklet on Mazindol, Nordwijkerhout, Netherlands, 1974
[5] Int. Symp. on Amphetamine and Related Compounds, Milano, 1970.
*ED$_{50}$ is the oral dose after administration of which, following a period of 24 hours of starvation, the rats consume the half amount of food as compared to control, or the oral dose after the administration of which the body weight gain is a half of that of control.

The chemical composition of the drugs used is follows:

D-amphetamine (Actedron, Benzedrine): D-benzeneethanamine sulphate

Mazindol (Sanorex, Terenac): 5-(4-chlorophenyl)-2,5-dihydro-3H-imidazo[2,1-a]isoindol-5-ol Fenfluramine (Ponderax, Ponderal, Pondimine): DL-N-ethyl-α-methyl-3-trifluoromethylbenzeneethanamine hydrochloride Chlorphentermine (Pre-State, Desopimon): α,α-dimethyl-4-chlorobenzeneethanamine hydrochloride Ia: 4-[(3-cyclopentyloxy-4-methoxyphenyl)methyl]-2-imidazolidinone From data of Table I it is clearly seen that in the course of the study on structure activity relationship of compounds having the general formula I, the novel compound (Ia) showed an anorexigenic effect which is much more intense than that of the anorexigenic drugs introduced so far. Similarly, the therapeutic ratio of Ia is more favourable than that of the best anorexigenic drugs introduced so far.

The anorexigenic drugs on the market at present are nearly without exception psychostimulants in character. On the contrary, the novel substances of general formula I have a weak sedative and weak hypotensive effect. These favourable side effects may render possible a more advantageous utilization. The compounds synthetized according to the invention can be used to produce pharmaceutical compositions in such a way that a 4-[(3,4-dialkoxyphenyl) alkyl]-2-imidazolidinone derivative having the formula I is transformed to a pharmaceutical composition together with non-toxic, neutral, pharmaceutically acceptable diluents and/or carrier substances, as is usual for formulation of pharmaceuticals.

The daily dose of the novel substances according to the invention as calculated for adults is 10 to 50 mg.

Further details of the invention are given in the following non-limiting Examples.

EXAMPLE 1

4-[(3-Phenylmethoxy-4-methoxyphenyl)methyl]-2-imidazolidinone

Step (a)

5-[(3-Phenylmethoxy-4-methoxyphenyl)methylene]-2,4-imidazolidinedione

A mixture of 24.43 g (100 moles) of 3-phenylmethoxy-4-methoxybenzaldehyde (Berichte 67, 1214/1934/), 10.01 g. (100 mmoles) of hydantoin, 38 ml of anhydrous acetic acid and 19.5 g of anhydrous sodium acetate is heated to 140° C. with shaking and the solution obtained is refluxed at 158°–162° C. for 2.5 hours, then cooled and poured into 250 ml of ice-water. The gum obtained becomes crystalline after 30 minutes. The crystals are filtered, washed successively with water, ethanol and ether and dried to give 14.75 g (45.5%) of the title compound, m.p. 249°–251° C.

Analysis for $C_{18}H_{16}N_2O_4$ (324.34): Calculated: C, 66.66%; H, 4.97%; N, 8.64%. Found: C, 66.33%; H, 5.22%; N, 8.45%.

Step (b)

5-[(3-Phenylethyl-4-methoxyphenyl)methyl]-2,4-imidazolidinedione 32.43 g (100 mmoles) of the product obtained in Example 1, step (a) are suspended in 200 ml of water, 13 ml of 10 N sodium hydroxide are added and then 342 g of 2% sodium amalgam are portionswise given to the mixture during 45 minutes while stirring at 50° C., and cooling eventually by ice-water to maintain a temperature of 50° to 58° C. The clear solution thus obtained is further stirred together with the sodium amalgam at 50° C. for 45 minutes. The solution is decanted from mercury and the latter one is washed twice with 30 ml of water. The collected aqueous phases are cooled to −10° C. and acidified by 60 ml of concentrated sulphuric acid while stirring and keeping the temperature below 50° C. After 10 minutes the precipitated crystals are filtered and washed twice with 100 ml of water and dissolved in 350 ml of chloroform. The organic layer is washed with sodium hydrogen carbonate solution until neutral, dried over anhydrous magnesium sulphate and evaporated in vacuo. After adding 300 ml of benzene to the residue, the evaporation is repeated and the residue is triturated with 80 ml of ether. After 30 minutes the crystals are filtered and washed with 30 ml of ether to give 23.62 g (72.4%) of the title compound, m.p. 147°–149° C.

Analysis for $C_{18}H_{18}N_2O_4$ (326.35): Calculated: C, 66.25%; H, 5.56%; N, 8.58%. Found: C, 66.25%; H, 5.61%, N, 8.39%.

Step (c)

4-[(3-Phenylmethoxy-4-methoxyphenyl)methyl]-2-imidazolidinone 19.0 g (500 mmoles) of lithium aluminium hydride are dissolved in 250 ml of anhydrous ether. To this solution, 32.64 g of the product obtained in Example 1, step (b) are stepwise added in small portions in the course of 30 minutes, while the suspension formed is refluxed. To the suspension 250 ml of tetrahydrofurane are added under stirring during 30 minutes. In course of the addition of tetrahydrofurane, the suspension violently boils and should be moderated by cooling in ice-water from time to time. After the addition of tetrahydrofurane the mixture is boiled for 30 minutes, then the excess of lithium aluminium hydride is decomposed by 100 ml of ethyl acetate under cooling, the mixture is poured into 1200 ml of ice-water while stirring, acidified by 200 ml of concentrated hydrochloric acid and extracted four times with 500 ml of chloroform. The collected organic phases are washed with 100 ml of water, dried over anhydrous magnesium sulphate and evaporated in vacuo. To the residue 300 ml of benzene are added and the evaporation is repeated. The oily residue is triturated with 100 ml of ether, the crystals obtained are filtered after 30 minutes, washed twice with 50 ml of ether and dried to give 26.03 g (83.4%) of title compound, m.p. 154°–157° C.; after recrystallization from isopropanol the melting point rises to 156°–158° C.

Analysis for $C_{18}H_{20}N_2O_3$ (312.37): Calculated: C, 69.21%; H, 6.45%; N, 8.97%. Found: C, 69.28%; H, 6.58%; N, 8.85%.

EXAMPLE 2

4-[(3-Cyclopentyloxy-4-methoxyphenyl)methyl]-2-imidazolidinone

Step (a)

3-Cyclopentyloxy-4-methoxybenzaldehyde

To the solution of 15.22 g (100 mmoles) of isovaniline in 125 ml of dimethylsulphoxide, 27 g of powdered anhydrous potassium carbonate are added. The suspension is stirred at 60° C. for 30 minutes and then 12.9 ml (120 mmoles) of cyclopentyl bromide are added at 60° C. during 60 minutes. Then the suspension is stirred at the same temperature 8 hours, cooled to 25° C. and poured into 500 ml of water. The aqueous emulsion is extracted four times with 100 ml of ether. The collected ethereal phases are washed twice with 20 ml of 1 N sodium hydroxide solution, dried over anhydrous magnesium sulphate and evaporated. To the oily residue 100 ml of benzene are added and the evaporation is repeated. The remained oil is fractionally distilled in vacuo to give 20.65 g (94%) of title compound, b.p. 136°–138° C./0.01 Hgmm.

Analysis for $C_{13}H_{16}O_3$ (220.28): Calculated: C, 70.89%; H, 7.32%. Found: C, 70.78%; H, 7.27%.

Step (b)

5-[(3-Cyclopentyloxy-4-methoxyphenyl)methylene]-2,4-imidazolidinedione

From 22.03 g (100 mmoles) of the product obtained in Example 2, step (a) and 10.01 g (100 mmoles) of hydantoin, by using the procedure described in Example 1, step (a) 13.95 g (46.1%) of the title compound are obtained, m.p. 223°–225° C.

Analysis for $C_{16}H_{18}N_2O_4$ (302.33): Calculated: C, 63.57%; H, 6.00%; N, 9.26%. Found: C, 63.15%; H, 5.93%; N, 9.15%.

Step (c)

5-[(3-Cyclopentyloxy-4-methoxyphenyl)methyl]-2,4-imidazolidinedione

Starting from 30.23 g (100 mmoles) of the product obtained in Example 2, step (b) and using the procedure described in Example 1, step (b) 20.82 g (68.5%) of the title compound are obtained, m.p. 149°–151° C.

Analysis for $C_{16}H_{20}N_2O_4$ (304.35): Calculated: C, 63.14%; H, 6.62%; N, 9.20%. Found: C, 63.15%; H, 6.74%; N, 9.05%.

Step (d)

4-[(3-Cyclopentyloxy-4-methoxyphenyl)methyl]-2-imidazolidinone

Starting from 30.43 g (100 mmoles) of the product obtained in Example 2, step (c) and using the procedure described in Example 1, step (c) 21.05 g (72.5%) of the title compound are obtained, m.p. 110°–113° C. After recrystallization from acetone the melting point rises to 115°–116° C.

Analysis for $C_{16}H_{22}N_2O_3$ (290.37): Calculated: C, 66.18%; H, 7.64%; N, 9.65%. Found: C, 66.10%; H, 7.80%; N, 9.62%.

EXAMPLE 3

4-[(3-Cyclopentyloxy-4-methoxyphenyl)methyl]-2-imidazolidinone

Step (a)

4-[(3-Hydroxy-4-methoxyphenyl)methyl]-2-imidazolidinone 31.24 g (100 mmoles) of the product obtained in Example 1, step (c) are dissolved in the hot mixture of 300 ml of tetrahydrofurane and 130 ml of methanol and the solution is hydrogenated at 40°–45° C. in the presence of 3 g of 10% palladium-on-charcoal. During 75 minutes, 100 mmoles of hydrogen are absorbed. The catalyst is filtered and washed three times with a hot mixture of 100 ml of chloroform and 100 ml of methanol and the filtrate is evaporated. To the residue 300 ml of benzene are added and the evaporation is repeated. The residue is triturated with 100 ml of ether, the crystals formed are filtered after 30 minutes and washed with 50 ml of ether to give 20.38 g (91.5%) of the title compound, m.p. 192°–202° C. After recrystallization from methanol the melting point rises to 206°–208° C. (According to the German Offenlegungsschrift No. 1,921,685, this melting point is 198°–199° C.)

Step (b)

4-[(3-Cyclopentyloxy-4-methoxyphenyl)methyl]-2-imidazolidinone

To the solution of 22.22 g (100 mmoles) of the product obtained in Example 3, step (a) in 220 ml of dimethylsulphoxide, 27 g of powdered anhydrous potassium carbonate are added and the suspension is stirred at 60° C. for 30 minutes, then 12.9 ml (120 mmoles) of cyclopentyl bromide are portionwise added during 60 minutes while the temperature is kept at 60° C. The suspension is further stirred at 60° C. for 20 hours, then cooled to 25° C. and poured into 800 ml of water. The aqueous emulsion is extracted four times with 400 ml of chloroform. The collected organic phases are washed twice with 50 ml of 1 N sodium hydroxide solution, dried over anhydrous magnesium sulphate and evaporated in vacuo. To the oily residue 200 ml of benzene are added and the evaporation is repeated. The residue is triturated with 150 ml of ether and the crystals obtained are filtered after 30 minutes and washed with 50 ml of ether to give 21.30 g (73.4%) of the title compound, m.p. 104°–107° C. After recrystallization from acetone this melting point rises to 115°–116° C. On the basis of its physical properties, this product is identical with the compound obtained in Example 2, step (d).

EXAMPLE 4

1,3-bis-Methoxycarbonyl-4-[(3-cyclopentyloxy-4-methoxyphenyl)methyl]-2-imidazolidinone 29.04 g (100 mmoles) of the product obtained in Example 2, step (d) are stirred with 40 ml of ethyl trichloroacetate in an oil bath of 180° C. The starting material is dissolved within a short period. The chloroform formed during the reaction is distilled off (about 15 minutes), the solution obtained is evaporated under vacuum and 200 ml of ether are added to the residue. The crystals obtained are filtered after 30 minutes and washed twice with 50 ml of ether to give 34.62 g (85.2%) of the title compound, m.p. 138°–140° C.

Analysis $C_{20}H_{26}N_2O_7$ (406.44): Calculated: C, 59.10%; H, 6.45%; N, 6.89%. Found: C, 59.06%; H, 6.52%; N, 6.92%.

EXAMPLE 5

4-[(3-Cyclopentyloxy-4-methoxyphenyl)methyl]-2-imidazolidinone

Step (a)

2-Cyano-3-(3-cyclopentyloxy-4-methoxyphenyl)-2-propenic acid ethyl ester

To a solution of 22.03 g (100 mmoles) of the product obtained in Example 2, step (a) in 50 ml benzene, 21.4 ml (200 mmoles) of ethyl cyanoacetate, 2 g of ammonium acetate and 2 ml of acetic acid are added. The solution obtained is distilled through a Claisen device and the benzene distilled off is retrieved. Within about 5 hours 200 ml of benzene are distilled off and added, respectively. On evaporation of the solution, the product becomes crystalline. After filtering the product is washed with 50 ml of hexane, then twice with 50 ml of ether and the residue is dissolved in 120 ml of chloroform. To the opalescent solution 10 g of anhydrous magnesium sulphate are added, the suspension is filtered and the filtrate evaporated under vacuum. To the residue 100 ml of benzene are added and the evaporation is repeated. To the remainder 100 ml of ether are added and the crystals precipitated are filtered and washed twice with 30 ml of ether to give 24.85 g (79.0%) of the title compound, m.p. 109°–110° C.

Analysis $C_{18}H_{21}NO_4$ (315.38): Calculated: C, 68.55%; H, 6.71%; N, 4.44%. Found: C, 68.53%; H, 6.67%; N, 4.57%.

Step (b)

α-Cyano-3-(3-cyclopentyloxy-4-methoxybenzenepropionic acid ethyl ester

A mixture of 31.54 g (100 mmoles) of the product obtained in Example 5, step (a) with 340 ml of methanol, 100 ml of tetrahydrofurane and 5 ml of acetic acid is hydrogenated in the presence of 5 g of 10% palladium-on carbon catalyst. After absorption of the theoretical amount of hydrogen (about 8 hours), the catalyst is filtered and the solution is evaporated under vacuum. After addition of 300 ml of benzene to the residue, the evaporation is repeated. The crystalline residue is taken up in 60 ml of hexane and filtered to give 29.72 g (93.8%) of the title product, m.p. 53°–55° C.

Analysis for $C_{18}H_{23}NO_4$ (317.39): Calculated: C, 68.12%; H, 7.30%; N, 4.41%. Found: C, 68.19%; H, 7.42%; N, 4.51%.

Step (c)

α-Cyano-3-cyclopentyloxy-4-methoxybenzenepropionic acid hydrazide

To the solution of 31.74 g (100 mmoles) of the product obtained in Example 5, step (b) in 100 ml of ethanol, 6.56 ml (132 mmoles) of hydrazine hydrate are added and the mixture is kept at 25° C. After about 60 minutes, the product becomes crystalline. The thick suspension is filtered and the crystals are washed twice with 150 ml of ether to give 28.61 g (94.51%) of the title compound, m.p. 149°–150° C.

Analysis for $C_{16}H_{21}N_3O_3$ (303.37): Calculated: C, 63.35%; H, 6.98%; N, 13.85%. Found: C, 63.46%; H, 7.06%; N, 13.82%.

Step (d)

[1-Cyano-2-(3-cyclopentyloxy-4-methoxyphenyl)-ethyl]-carbamic acid methyl ester 30.34 g (100 mmoles) of the product obtained in Example 5, step (c) are suspended in 250 ml of 1 N $H_2SO_4$. To this suspension 7.60 g (110 mmoles) of sodium nitrite dissolved in 16 ml of water are added during 60 minutes, while the temperature is kept at 0°–5° C. The mixture is stirred at the same temperature for 30 minutes, then 200 ml of dichloromethane are added and stirred at the same temperature for 15 minutes further, then separated, and the aqueous phase is extracted twice with 40 ml of dichloromethane. The collected organic phases are washed twice with 30 ml of water and dried over anhydrous magnesium sulphate. To the solution 350 ml of methanol are added, then dichloromethane and a part of methanol are distilled off through a Raschig device of 30 cm in length. The methanol solution, which is about 150 ml, is refluxed for 4 hours, then the solution is evaporated under vacuum. To the residue 150 ml of isopropanol are added and the evaporation is repeated. The residue is recrystallized from 80 ml of isopropanol to give 27.82 g (87.52%) of the title product, m.p. 121°–122° C.

Analysis(for $C_{17}H_{22}N_2O_4$ (318.38): Calculated: C, 64.13%; H, 6.97%; N, 8.80%. Found: C, 64.19%; H, 6.84%; N, 8.87%.

Step (e)

2-Amino-1-[(3-cyclopentyloxy-4-methoxyphenyl)ethyl]-carbamic acid ethyl ester hydrochloride The solution of 31.84 g (100 mmoles) of the product obtained in Example 5, step (d) in 600 ml of methanol is hydrogenated in the presence of 15 g of Raney cobalt and 10 ml of triethylamine at a pressure of 100–120 atm. at 100°–110° C. After hydrogenation for 12 hours the catalyst is filtered out and the solution is evaporated under vacuum. The residue is dissolved in 160 ml of ethyl acetate and the pH of the solution is adjusted to 2.5–3.0 by means of 5 M ethanolic hydrogen chloride solution. The crystalline suspension is cooled at 0° C. overnight and filtered. The crystals are washed with 100 ml of acetone and then with 100 ml of ether to give 25.12 g (64.34%) of the title compound, m.p. 155°–158° C.

Analysis for $C_{17}H_{26}N_2O_4 \cdot HCl$ (358.87): Calculated: C, 56.90%; H, 7.58%; N, 7.81%. Found: C, 56.79%; H, 7.70%; N, 7.69%.

Step (f)

4-[(3-Cyclopentyloxy-4-methoxyphenyl)methyl]-2-imidazolidinone 35.89 g (100 mmoles) of the product obtained in Example 5, step (e) are stirred with 350 ml of 3 N sodium hydroxide solution at 90°–95° C. for 60 minutes, then kept at 25° C. overnight. The crystals are filtered, washed twice with 100 ml of water, twice with 100 ml of isopropanol and with 100 ml of ether to give 22.41 g (77.32%) of the title compound, m.p. 107°–111° C. After recrystallization from acetone the melting point rises to 114°–115.5° C. On the basis of physical properties, this product is identical with that obtained in Example 2, step (d).

EXAMPLE 6

Oral tablets containing 10 mg of active ingredient are prepared with the following composition:

| | |
|---|---|
| 4-[(3-Cyclopentyloxy-4-methoxyphenyl)methyl]-2-imidazolidinone | 0.010 g |
| Wheat starch | 0.042 g |
| Milk sugar | 0.037 g |
| Carboxymethylcellulose | 0.006 g |
| Talc | 0.005 g |
| Average weight of one tablet: | 0.100 g |

What we claim is:

1. 1,3-bis-methoxycarbonyl-4-[(3-cyclopentyloxy-4-methoxyphenyl)methyl]-2-imidazolidinone.

2. A method of inducing anorexia in a human in need of the same, comprising administering to said human by the oral route 10 to 50 mg per day of a compound having the formula

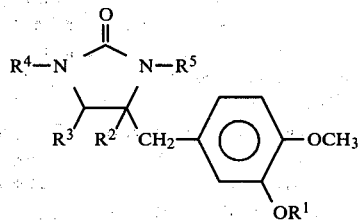

wherein
$R^1$ stands for a cycloalkyl group containing from 3 to 6 carbon atoms or benzyl group;
$R^2$ stands for hydrogen atom or an alkyl group containing from 1 to 4 carbon atoms;
$R^3$ stands for hydrogen atom or an alkyl group containing from 1 to 4 carbon atoms;
$R^4$ stands for hydrogen atom, or an alkyl group containing from 1 to 4 carbon atoms or an alkoxycarbonyl group containing from 2 to 4 carbon atoms; and
$R^5$ stands for hydrogen atom or $R^4$ when $R^4$ is an alkoxycarbonyl group containing from 2 to 4 carbon atoms.

* * * * *